Jan. 19, 1965 J. J. GRULLEMANS Plant Pat. 2,467
HOSTA PLANT
Filed Jan. 3, 1963
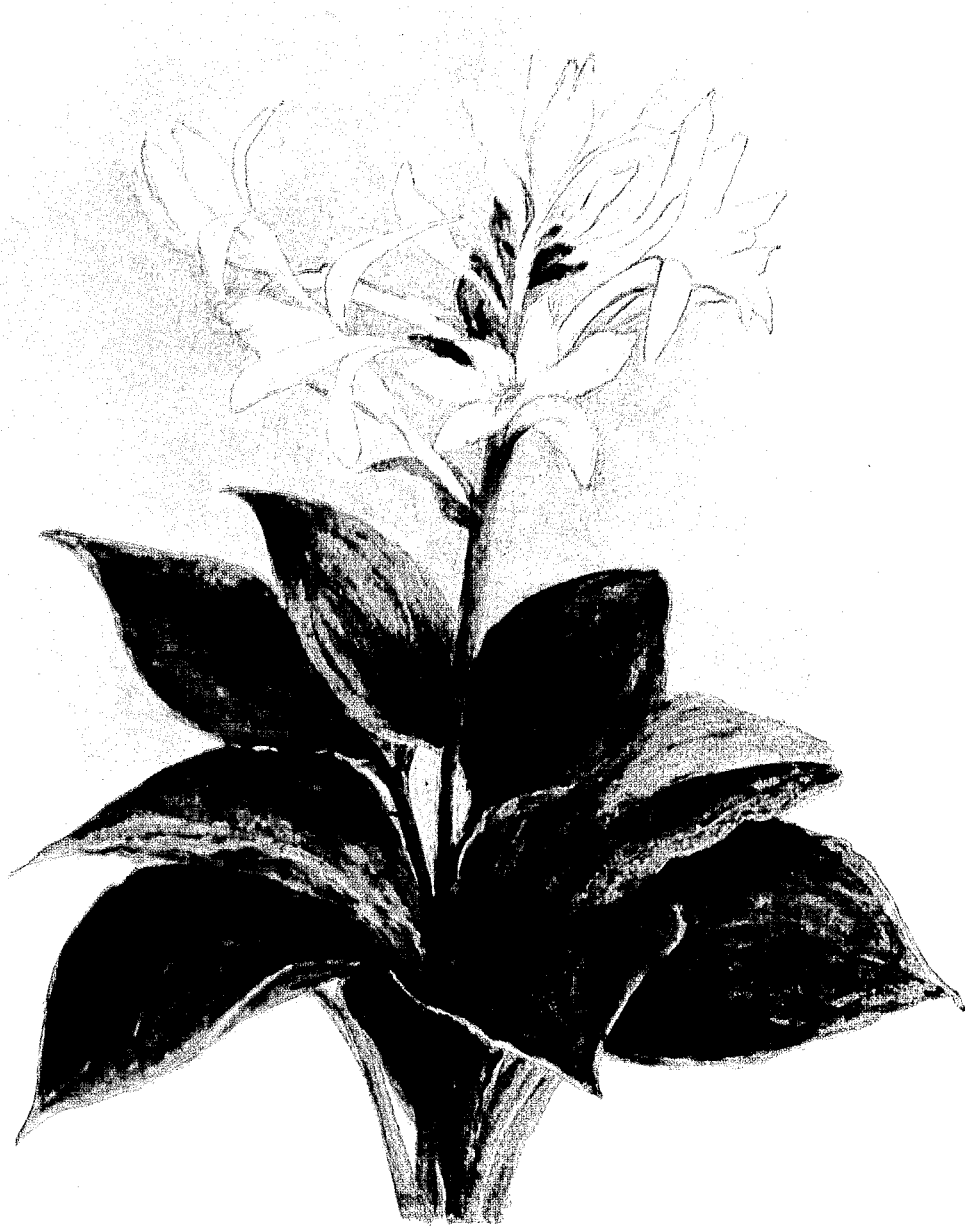
INVENTOR
John J. Grullemans,
by: John H. Lunsford,
his ATTY.

United States Patent Office

Plant Pat. 2,467
Patented Jan. 19, 1965

2,467
HOSTA PLANT
John James Grullemans, Harwichport, Mass.
Filed Jan. 3, 1963, Ser. No. 249,303
1 Claim. (Cl. Plt.—68)

This invention relates to a new variety of Hosta or Funkia plant.

The present plant was produced originally by me by the deliberate crossing of a *Hosta plantaginea,* also known as a *Hosta* or *Funkia subcordata grandiflora* plant as a seed parent with a *Hosta* or *Funkia sieboldiana* plant as the pollen parent.

The new variety was asexually reproduced by me at Mentor, Ohio, by root division.

The drawing shows in color a typical flower stalk, and leaves.

The new variety is a herbaceous, hardy perennial of generally dense and clumped growth. The flower stalks grow generally to a height of about 30 inches in a three year old plant. It grows more vigorously than either parent.

The exposed portion of the plant has exceptional resistance to low temperatures when protected and unprotected. Its resistance to drought is good, and to wet seasons is exceptional. It is hardier than the pistillate parent and compares in hardiness with the staminate parent.

For growth it prefers moderate sun or partial shade, and is indifferent to exposure and drainage. It prefers heavy soil, but responds favorably in reasonably light soil.

The roots are a fibrous mass similar to those of the staminate parent. They are large for this type of plant.

The main stalks of the plant are of the usual appearance and greenish brown color, comparable in both appearance and color to those of the parents.

The foliage in general has a compact appearance. The leaf arrangement is basal. Both new and old leaves are light green, on the top and bottom, resembling in color the colors of the leaves of the parents. In general, the color of the leaves is uniform.

The leaves are relatively large, ranging from 10 to 15 inches in length and from 4 to 7 inches in width, being intermediate between the sizes exhibited by the parents. In shape, they are ovate, with entire margins, obtuse to acute bases, and acuminate to acute apices. They are of medium thickness with smooth upper and lower faces. Their persistency on the plant is excellent. An unusual feature of the leaves is that they retain their color and vigor well in full sunlight, whereas neither parent does.

The petioles or leaf stems are light green. They have a smooth surface texture, and vary in strength from strong to usual. Their average length is about the same as that of the *Hosta sieboldiana.*

The plant grows and blooms well in north temperate regions and can be grown throughout the United States. An unusual characteristic is that it thrives and blooms well in sun or shade. It prefers wet, hot seasons, and rich loam or clay loam; whether acid, alkaline, or neutral.

The plant blooms continuously from about August 15 through October 15. It produces an excellent bloom under all growing conditions, neither the size nor color being altered. Cutting of blooms eliminates blooming for the season.

The buds are of the usual size and shape and borne in the usual manner for Hosta plants. The petal color, when sepals first divide, is white and continues so when the petals begin to unfurl, and when they are half blown.

The sepals and calyx are of the usual shape and size.

The peduncles average from 24 to 30 inches in length and have the usual surface texture and color.

The pedicels have the usual length, texture, color and strength.

The blooms average from 1½ to 2 inches in diameter. An average plant will bear about 12 flowering stalks, with 6 to 8 flowers per stalk. The blooms are borne in short racemes. Their permanence is good on the plant and when cut.

The petalage is white throughout, from the base to the tips of the petals, and on both faces.

The general tonality of the plant from a distance, when it is in bloom, is white. There is no change during the blooming season.

The petals are smooth textured, tubular, and six-lobed. There are no petaloids. The persistence of the petals is good, both for cut and uncut blooms.

The fragrance of the blooms is usual for *subcordata grandiflora* types. It is strong and definitely fragrant, but not quite as fragrant as the *plantaginea.* Its lasting quality is excellent for both cut and uncut blooms.

The stamens, filaments, pollen, styles and stigmas are about the same as those of the *Hosta sieboldiana.*

The ovaries are sparse, and the plant does not set seed.

The drawing further illustrates the characteristics of the variety and the following tabulation is a detailed description of the new variety:

*General*

Parentage:
- *Seed parent.*—*Hosta* or *Funkia plantaginea,* also known as *Funkia subcordata grandiflora.*
- *Pollen parent.*—*Hosta* or *Funkia sieboldiana.*

Classification: Botanic—Hosta or Funkia hybrid.

*Flower*

Blooming habit: Flowering—continuous from about August 15 until October 15.

Bud:
- *Size.*—1½ to 2 inches in diameter.
- *Form.*—Usual.
- *Color.*—When sepals first divide, petals are white, when petals begin to unfurl they are white, and when half blown, they are white, when full blown, they are white.
- *Sepals.*—Usual.
- *Calyx.*—Usual; aspect, usual.
- *Peduncle.*—Length, from 24 to 30 inches.
- *Aspect.*—Usual.
- *Color.*—Usual; strength, usual.
- *Opening.*—Usual.

Bloom:
- *Size.*—1½ to 2 inches in diameter.
- *Borne.*—In short racemes.
- *Stems.*—12 flowering stalks per plant, 6 to 8 flowers on each.
- *Permanence.*—On the plant, usual.

Petalage: Petals are tubular and six-lobed.
- *Color.*—White throughout.
- *Variegations.*—No changes in color during the blooming season.

Petals:
- *Texture.*—Smooth.
- *Form and arrangement.*—Tubular, six-lobed, usual for *subcordata grandiflora* type.
- *Petaloids in center.*—None.
- *Persistence.*—Good.
- *Fragrance.*—Strong. Definitely fragrant but not quite as fragrant as *plantaginea* or *subcordata grandiflora.*
- *Lasting quality.*—On plant and when cut, excellent.

Genital organs:
- *Stamens.*—About the same as those of the *Hosta sieboldiana.*

*Color.*—About the same as those of the *Hosta sieboldiana.*

*Arrangement.*—About the same as those of the *Hosta sieboldiana.*

*Filaments.*—About the same as those of the *Hosta sieboldiana.*

*Color.*—About the same as those of the *Hosta sieboldiana.*

*Pollen.*—About the same as those of the *Hosta sieboldiana.*

*Styles.*—About the same as those of the *Hosta sieboldiana.*

*Stigmas.*—About the same as those of the *Hosta sieboldiana.*

*Ovaries.*—Medium size and sparse, do not set seed.

*Plant*

Form: Herbaceous, hardy, compact, clumped perennial.

Growth: More vigourous than parents.

Foliage: Compact and basal.

*Size.*—Large 10 to 15 inches length, and 4 to 7 inches in width, and medium in thickness.

*Quantity.*—Average.

*Color.*—New and old leaves, light green, resembling *plantaginea* or *subcordata grandiflora* parent; uniform throughout.

*Shape.*—Ovate; base obtuse to acute; apex acuminate to acute.

*Texture.*—Smooth on both faces.

*Margin.*—Entire.

*Leaves.*—Hold color and vigor well in full sunlight whereas neither parent does.

Petiole:

*Length.*—Average about same as *sieboldiana,* shorter than *plantaginea* or *subcordata grandiflora*; strong to usual.

*Color.*—Light green, usual.

Stipules: None.

Disease resistance: Appears to have better than average resistance to Hosta diseases.

Wood: Leaf and flower stalks, usual green color and smooth texture.

The most distinctive features and characteristics of the plant are as follows:

This new variety of plant has the desirable characteristics of both parents without their undesirable ones. It is somewhat smaller than the *plantaginea* or *subcordata grandiflora,* but larger than the *sieboldiana.* It has the great vigor and extreme hardiness of *sieboldiana* with the fine quality, flagrant flowers of *plantaginea* or *subcordata grandiflora.*

Further, its foliage does not burn when the plant is grown in full sunlight and it blooms well in sun or shade, as distinguished from prior Hosta plants which require shade or partial shade for normal growth and bloom.

It thrives in sunlight, a quality which extends its use to sunny borders, greatly enhancing its usefulness in plantings.

It has the same flowering and foliage effect as *plantaginea* or *subcordata grandiflora,* which cannot withstand cold winters without careful protection and which is difficult to transplant, yet the present plant is very vigorous and hardy in exposed locations, and very easy to transplant.

It increases in size rapidly.

Having shown and described my new variety of Hosta or Funkia plant and its manner of asexual reproduction, I claim:

The new and distinct variety of Hosta or Funkia plant herein illustrated and described.

No references cited.